United States Patent [19]

Thomas et al.

[11] Patent Number: 5,426,258
[45] Date of Patent: Jun. 20, 1995

[54] PROCESS FOR REDUCING THE AGGLOMERATION TENDENCY OF HYDRATES IN THE PRODUCTION EFFLUENT

[75] Inventors: Michel Thomas, Rueil Malmaison; Anne-Sophie Baley, Paris; Jean-Pierre Durand, Chatou, all of France

[73] Assignee: Institut Francais du Petrole, Rueil-Malmaison, France

[21] Appl. No.: 139,666

[22] Filed: Oct. 22, 1993

[30] Foreign Application Priority Data

Oct. 23, 1992 [FR] France ............................ 92 12836

[51] Int. Cl.[6] .......................... C07C 7/20; C10G 33/04
[52] U.S. Cl. ..................................... 585/15; 208/188
[58] Field of Search ................ 208/187, 188; 585/15, 585/867; 95/153

[56] References Cited

U.S. PATENT DOCUMENTS

| | | | |
|---|---|---|---|
| 2,978,026 | 4/1961 | Bemis | 166/44 |
| 2,979,528 | 4/1961 | Lundsted | 260/584 |
| 3,185,217 | 5/1965 | Brooks, Jr. et al. | 166/42 |
| 4,973,775 | 11/1990 | Sugier et al. | 585/15 |

FOREIGN PATENT DOCUMENTS

| | | |
|---|---|---|
| 0323307 | 7/1989 | European Pat. Off. |
| 0323774 | 7/1989 | European Pat. Off. |
| 2036594 | 7/1980 | United Kingdom |
| 2216573 | 10/1989 | United Kingdom |

OTHER PUBLICATIONS

Chemical Abstracts, vol. 106, No. 16, Apr. 1987, p. 190, col. 2 (abstract of SU-A-2, 965,596 to Kuliev et al.).

*Primary Examiner*—Asok Pal
*Assistant Examiner*—Bekir L. Yildirim
*Attorney, Agent, or Firm*—Millen, White, Zelano, & Branigan

[57] ABSTRACT

A description is given of a process for reducing the agglomeration tendency of hydrates within a fluid incorporating at least water and hydrocarbons, liable to form hydrates, under conditions where said hydrates may form, characterized in that into said fluid is incorporated an alkylene oxide-based hydrosoluble polymer or copolymer containing at least one $-(OR)-_n$ sequence, in which R represents a hydrocarbon group having 2 or 3 carbon atoms and n represents the average degree of polymerization of said sequence, at least one of the $-(OR)-_n$ sequences being an ethylene polyoxide sequence, associated with a thermodynamic inhibitor of the formation of hydrates, e.g. an alcohol or a glycol. This process is particularly appropriate for the case where the fluid to be treated contains a high proportion of water, e.g. more than 30% by weight. The presence of salts in the water can at least partly dispense with the addition of alcohols or glycols.

17 Claims, No Drawings

PROCESS FOR REDUCING THE AGGLOMERATION TENDENCY OF HYDRATES IN THE PRODUCTION EFFLUENT

BACKGROUND OF THE INVENTION

The invention relates to a process for reducing the agglomeration tendency of hydrates of natural gases, petroleum gases or other gases by the use of at least one additive. The gases which form hydrates can in particular incorporate at least one hydrocarbon chosen from among methane, ethane, ethylene, propane, propene, n-butane and isobutane and optionally $H_2S$ and/or $CO_2$.

These hydrates form when water is present with the gas, either in the free state, or dissolved in a liquid phase, such as a liquid hydrocarbon, and when the temperature reached by the mixture, particularly of water, gases and optionally liquid hydrocarbons, such as oil, drops below the thermodynamic temperature for the formation of hydrates, said temperature being given for a known gas composition and when the gas pressure is fixed.

Hydrate formation is feared, particularly in the oil and gas industries, where the conditions for the formation of hydrates frequently occur. Thus, in order to reduce the production costs of crude and gas, both with respect to the capital costs and with regards to the operating costs, one way considered, particularly in the case of ocean production, is to reduce or eliminate the treatments applied to the crude or gas to be transported from the field to the coast and to leave all or part of the water in the fluid to be transported. These ocean treatments generally take place on a platform located on the surface in the vicinity of the field, so that the initially hot effluent can be treated prior to the reaching of the thermodynamic conditions for the formation of hydrates as a result of the cooling of the effluent by the ocean water.

However, as occurs in practice, when the thermodynamic conditions necessary for the formation of hydrates are combined, the agglomeration of the hydrates leads to the filling and blocking of the transportation pipes by the creation of plugs, which prevent any passage of gas or crude oil.

The formation of hydrate plugs can lead to a production stoppage and therefore cause considerable financial losses. Moreover, putting back into service of the installation, particularly in the case of ocean transportation or production, can take a long time, because it is very difficult to decompose the hydrates formed. Thus, when the production of an underwater field of natural gas or oil and gas containing water reaches the surface and is then transported to the ocean bed, as a result of the lowering of the temperature of the effluent produced, thermodynamic conditions are combined so that hydrates form, agglomerate and block the transfer pipes. The temperature at the ocean bed can e.g. be 3° or 4° C.

Favorable hydrate formation conditions can also occur in the same way on land, in the case of pipes which are either not buried or not buried sufficiently deeply, e.g. when the ambient air temperature is low.

In order to obviate these disadvantages, the prior art has sought to use products which, added to the fluid, could act as inhibitors by lowering the thermodynamic hydrate formation temperature. They are in particular alcohols, such as methanol, or glycols, such as mono-, di- or tri-ethylene glycol. This solution is very onerous, because the inhibitor quantity to be added can reach 10 to 50% of the water content and these inhibitors are difficult to recover in a complete manner.

It has also been recommended that the transportation pipes be insulated in such a way as to prevent the temperature of the transported fluid from reaching the hydrate formation temperature under operating conditions. However, such a procedure is also very expensive.

In addition, various anionic or nonionic surfactants have been tested for their effect in delaying the formation of hydrates within a fluid containing a gas, particularly a hydrocarbon, and water. Reference can e.g. be made to the article by Kuliev et al "Surfactants studied as hydrate-formation inhibitors" Gazovoe Delo No. 10, 1972, pp. 17 to 19, reported in Chemical Abstracts 80, 1974, 98122r.

A description has also been given of the use of additives able to modify the hydrate formation mechanism, because instead of rapidly agglomerating with one another and forming very solid plugs, the hydrates formed disperse in the fluid without agglomerating and without obstructing the pipes when the temperature of the transported fluid is not too low.

Reference can be made in this connection to patent application EP-A-323,774 in the name of the present applicant, which describes the use of nonionic amphiphilic compounds chosen from among esters of polyols and carboxylic acids, in substituted or unsubstituted form, and compounds having an imide function. Patent application EP-A-323,775, also in the name of the applicant, describes the use of compounds belonging to the family of diethanol amides of fatty acids or fatty acid derivatives, U.S. Pat. No. 4,856,593 describes the use of surfactants, such as organic phosphonates, phosphate esters, phosphonic acids, their salts and esters, inorganic polyphosphates and their esters, as well as polyacrylamides and polyacrylates. Patent application EP-A-457,375 describes the use of anionic surfactants, such as alkyl aryl sulphonic acids and their alkali metal salts.

These compounds are suitable when the liquid phase is formed from water and liquid hydrocarbons, such as e.g. a condensate or an oil, but are less satisfactory when the liquid phase is constituted in majority or sole manner by water (case of dry gases).

SUMMARY OF THE INVENTION

It has now been discovered that the combination of alkylene oxide-based polymers and copolymers, which have hitherto not been used for this purpose, and a hydrate formation inhibitor used in a smaller concentration than that necessary for inhibiting any hydrate formation, is very effective for the modification of the hydrate formation mechanism, while still limiting the quantity of hydrates formed and their tendency to agglomerate.

This modification of the hydrate crystal formation mechanism can be utilized for the transportation of fluids forming hydrates, particularly in the case where the water content in the liquid phase is high. Thus, it has been observed that, in the presence of the additives according to the invention, once the crystals have formed, instead of agglomerating with one another and forming very solid plugs or deposits in the equipment where the fluid circulates, they remain in dispersed form over a wide temperature range, below the thermodynamic equilibrium temperature at the considered pressure.

When a gas-water mixture is exposed to a temperature, which is lower than the thermodynamic equilibrium temperature, there is a relatively rapid thickening of the fluid up to the formation of a solid plug rendering the circulation of the fluid difficult or even impossible. The addition of the additives according to the invention combined with a thermodynamic inhibitor in a low or moderate concentration, particularly when the water content in the liquid phase is high, gives rise to a modification in the formation of the hydrates, i.e. instead of solid plugs forming, the formation of small crystals is observed.

Therefore the present invention proposes a process for reducing the agglomeration tendency of hydrates within a fluid incorporating at least water and hydrocarbons liable to form hydrates, under temperature and pressure conditions where hydrates can form, characterized in that into said fluid is incorporated an alkylene oxide-based hydrosoluble polymer or copolymer, combined with a thermodynamic hydrate formation inhibitor, the latter being used in a concentration below that which would be necessary for inhibiting all hydrate formation under the pressure and temperature conditions encountered.

The thermodynamic inhibitor used can in particular be methanol, mono-, di- or tri-ethylene glycol. The salts optionally contained in the water produced can also fulfil this function. The inhibitor makes it possible to limit the hydrate quantity which can form within the liquid effluent.

This combination is of interest when the liquid phase is in the majority or totally constituted by water. Thus, in the absence of an inhibitor and after the formation of hydrates, the residual liquid phase quantity will be too low to ensure the transportation thereof. The inhibitor quantity to be introduced could be equivalent at the most to ⅔ and preferably to approximately half the minimum quantity necessary for preventing hydrate formation under the pressure and temperature conditions encountered and for the fluid in question. However, said content could be optimized as a function of the dispersing additive quantity jointly used.

The polymers and copolymers used in the invention for delaying the formation and reducing the tendency to agglomeration of hydrates can be more particularly defined by the fact that they contain one or more —(O-R)—$_n$ sequences, in which R represents a hydrocarbon group having 2 or 3 carbon atoms and n represents the average degree of polymerization, which can be calculated on the basis of the molecular weight of the hydrosoluble polymer or copolymer, and at least one of the —(OR)—$_n$ sequences is an ethylene polyoxide sequence —(CH$_2$—CH$_2$—O)—$_n$.

Preferably, the polymers and copolymers according to the invention are obtained from ethylene oxide and optionally propylene oxide, for example polyethylene glycols of general formula:

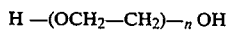

obtained by the reaction of ethylene oxide with ethylene glycol or water, a monoether, such as the monomethyl ether of said polyethylene glycols or sequenced copolymers of ethylene oxide and propylene oxide, in which the proportion of ethylene oxide units preponderates compared with that of the propylene oxide units. Such sequenced copolymers can e.g. be obtained by the condensation of ethylene oxide on a polypropylene glycol. Such sequenced copolymers can also be obtained by the condensation of propylene oxide on an ethylene diamine molecule, followed by ethylene oxide condensation.

The ethylene oxide content in these different copolymers must be adequate to obtain hydrosoluble copolymers and will e.g. exceed approximately 20% by weight and preferably exceeds approximately 50% by weight.

The molecular weight of the polymers and copolymers used in the invention is variable and can be between 1000 and 30,000.

All these compounds can be used singly or in mixed form and optionally associated with other compounds, e.g. surfactants.

The use according to the invention of the polymers and copolymers as described hereinbefore is particularly advantageous from the economic standpoint, because these products are used in very small concentrations, generally below 2% by weight, e.g. 0.1 to 2% by weight and preferably 0.2 to 1% by weight, based on water, and because the cost of these products is low.

In the case where addition takes place to the fluid, as the thermodynamic hydrate formation inhibitor, of an alcohol or a glycol, the content of the latter can e.g. range up to 20% by weight based on the water and preferably up to 10% by weight.

In the case where the fluid comprises seawater or formation water e.g. having a salt content exceeding 20 g/l, there is no need to add alcohol or glycol, the salts, e.g. sodium chloride serving as the inhibitor.

A particularly advantageous use of the polymers and copolymers according to the invention relates to the case where the mixture of water and liquid hydrocarbons contains a water content equal to or above 30% and preferably in excess of 50% by volume.

Examples

In order to evaluate the effectiveness of the considered hydrosoluble additives on the formation conditions and maintaining in suspension or delaying of agglomeration, in the following examples tests concerning the formation of hydrates on the basis of methane and water were carried out, optionally in the presence of a light condensate and/or a conventional thermodynamic inhibitor such as methanol.

The equipment used for these tests comprises a sapphire visual cell with an internal volume of 90 cm$^3$, able to operate at a maximum pressure of 150 bars. This cell is located in a thermocontrolled enclosure, in which it is possible to maintain the temperature constant, or bring about a programmed temperature drop. The temperature and pressure in the cell are measured by two sensors. Stirring within the cell takes place by means of a blade stirrer, able to rotate at a constant speed by magnetic driving. The value of the torque for maintaining this constant speed during the formation of hydrates can be linked indirectly with the viscosity of the medium.

A buffer bottle containing methane is permanently connected to the aforementioned cell by one of its ends, and to a positive displacement pump by the other. By the injection of mercury into the buffer bottle, this pump makes it possible to displace the methane volume necessary for keeping the pressure constant in the bottle and in the cell, so as to compensate the pressure drop due to gas consumption during the formation of hydrates. The measurement of the mercury volume introduced makes it possible to know the consumed gas quantity, i.e., by ignoring volume variations, the hydrate quantity formed as a function of the time or temperature.

Initially, the cell contains 40 cm³ of distilled water, contains no additive or containing the additive to be tested, and gas (methane), while being permanently connected to the buffer bottle. The pressure for each test is fixed and kept constant at 80 bars throughout the test duration. The initial temperature is 20° C.

In order to assess the effectiveness of the additives, the temperature is lowered to the temperature of the experiment and accompanied by constant stirring. If hydrate crystals appear mercury is injected into the buffer cell containing the gas, in order to keep the pressure constant, so as to compensate the gas consumption due to the formation of hydrate crystals. The injected gas volume compensates the temperature drop effect and the consumption due to the formation of hydrates. It can be linked with the quantity of hydrates formed. The torque value is also recorded throughout the test. When hydrate crystals agglomerate, the stirrer becomes completely blocked.

The initial value of the torque is 17.5 mN.m for a stirrer rotation speed of 300 r. p. m. The dissociation temperature of the methane hydrates at 80 bars is 10.7° C. in the presence of pure water and 5.9° C. in the presence of water with 10% by weight methanol. In order to prevent hydrate formation at 80 bars and 2° C. (conditions for the experiments), it is necessary to add approximately 17% by weight methanol to the water.

Between two consecutive tests the cell is cleaned with distilled water, then methanol and is finally dried. The maximum test duration is 8 hours.

The following examples illustrate the invention without limiting its scope. Examples 1, 2, 3, 5, 6 and 7 are given for comparison purposes.

Example 1 (Comparative)

In this example working takes place with 40 cm³ of distilled water and methane, with no additive. The pressure is fixed at 80 bars and the temperature at 2° C., as a function of the experimental protocol described hereinafter. Under these conditions, the stirrer blocked 15 minutes after the start of hydrate formation, The consumed gas volume is 38.6 cm³.

Example 2 (Comparative)

In this example the procedure of example 1 was used, with the same gas and the same water and under the same pressure, but to the water was added 0.5% by weight of ethylene oxide-propylene oxide copolymer obtained by the condensation of propylene oxide on a molecule of ethylene diamine, followed by the condensation of ethylene oxide, said copolymer having an average molecular weight of 26,000 and containing 80% by weight of ethylene oxide.

Under these conditions, the stirred blocked 1.5 hour after the start of hydrate formation. The consumed gas volume is 35.1 cm³.

Example 3 (Comparative)

The procedure of example 1 was followed, but 10% by weight methanol was added to the water. Under these conditions the stirrer blocked 4 hours after the start of hydrate formation. The consumed gas volume is 36.4 cm³.

Example 4

The procedure of example 1 was used, but to the water were added 10% by weight methanol and 0.5% by weight of the copolymer used in example 2. Under these conditions there was a slight increase in the torque value, which stabilized at 18.6 mN.m during 8 hours. The consumed gas volume is 36.5 cm³.

Example 5 (Comparative)

The procedure of example 1 was followed, but the starting product was 30 cm³ of water and 10 cm³ of a light North Sea condensate, without any additive. Under these conditions, there was a progressive deposition of hydrates on the walls of the cell and a stirrer blockage 0.75 hour after the start of hydrate formation. The consumed gas volume is 33.7 cm³.

Example 6 (Comparative)

The procedure of example 5 was followed, but starting with 30 cm³ of water and 10 cm³ of a light North Sea condensate. 0.5% by weight, based on the water, of polyethylene glycol monomethyl ether was added, said product having an average molecular weight close to 5000. Under these conditions there was an increase in the torque value, which stabilized at 29.5 mN.m after 5 hours and a blockage occurred after 7 hours. The added gas volume is 32.6 cm³.

Example 7 (Comparative)

The procedure of example 5 was used, but 10% by weight methanol were added to the water. Under these conditions the stirrer blocked 3.5 hours after the start of hydrate formation. The added gas volume is 33.9 cm³.

Example 8

The procedure of example 6 was used, but 10% by weight methanol were added to the water. Under these conditions the torque value rose and stabilized at 19.5 mN.m after 6 hours, without stirrer blockage. The injected gas volume is 34.6 cm³.

Example 9

If in example 8 only 0.2% by weight, based on the water, of polyethylene glycol monomethyl ether was added, there was a torque value increase, which stabilized at 25.3 mN.m after 4 hours without stirrer blockage. The injected gas volume is 32.8 cm³.

Example 10

Operation was in accordance with example 2, but using salt water (50 g/l NaCl). Under these conditions, there was an increase in the torque value, which stabilized at 24.5 mN.m after 4 hours without stirrer blockage. The consumed gas volume is 31.9 cm³.

We claim:

1. A process for reducing the agglomeration tendency of hydrates within a fluid containing at least water and hydrocarbons able to form hydrates, under conditions where said hydrates can form comprising incorporating into said fluid a thermodynamic hydrate formation inhibitor and an alkylene oxide-based hydrosoluble polymer or copolymer containing at least one —(OR)—$_n$ sequence, in which R represents a hydrocarbon group having 2 or 3 carbon atoms and n represents the average degree of polymerization of said sequence, at least one of the —(OR)—$_n$ sequences being an ethylene polyoxide sequence, and the ethylene oxide content of the polymer or copolymer exceeds 50% by weight, based on the polymer or copolymer.

2. A process according to claim 1, wherein said hydrosoluble polymer is a polyethylene glycol.

3. A process according to claim 1, wherein said hydrosoluble polymer is a polyethylene glycol monoether.

4. A process according to claim 1, wherein said hydrosoluble copolymer is a sequenced copolymer of ethylene oxide and propylene oxide in which the proportion of ethylene oxide units preponderates compared with that of the propylene oxide units.

5. A process according to claim 4, wherein said hydrosoluble copolymer is obtained by the condensation of ethylene oxide on a polypropylene glycol.

6. A process according to claim 4, wherein said hydrosoluble copolymer is obtained by the condensation of propylene oxide on an ethylene diamine molecule followed by ethylene oxide condensation.

7. A process according to claim 1, wherein the molecular weight of said hydrosoluble polymer or copolymer is between 1000 and 30,000.

8. A process according to claim 1, wherein said hydrosoluble polymer or copolymer is used in a concentration of 0.1 to 2% by weight, based on the water present.

9. A process according to claim 1, wherein the thermodynamic hydrate formation inhibitor is methanol, mono-, di- or tri-ethylene glycol.

10. A process according to any one of the claim 1, wherein the inhibitor concentration in the aqueous phase is below $\frac{2}{3}$ of the concentration necessary for completely inhibiting hydrate formation.

11. A process according to any one of the claim 1, wherein the inhibitor concentration is at the most 20% by weight, based on the water.

12. A process according to claim 1, wherein the water present in the fluid contains at least one salt such as sodium chloride, said salt functioning as at least part of the thermodynamic inhibitor.

13. A process according to claim 1, wherein the water represents at least 30% by volume of the mixture of water and liquid hydrocarbons.

14. A process according to claim 2, wherein the thermodynamic hydrate formation inhibitor is methanol, mono-, di-, or tri-ethylene glycol.

15. A process according to claim 3, wherein the thermodynamic hydrate formation inhibitor is methanol, mono-, di-, or tri-ethylene glycol.

16. A process according to claim 4, wherein the thermodynamic hydrate formation inhibitor is methanol, mono-, di-, or tri-ethylene glycol.

17. A process according to claim 1, wherein the ethylene oxide content of the polymer or copolymer is at least 80%, based on the polymer or copolymer.

* * * * *

UNITED STATES PATENT AND TRADEMARK OFFICE
CERTIFICATE OF CORRECTION

PATENT NO. : 5,426,258
DATED : June 20, 1995
INVENTOR(S) : Michel THOMAS et al.

It is certified that error appears in the above-indentified patent and that said Letters Patent is hereby corrected as shown below:

Claim 11; column 8, line 8: After "according to" delete " any one of the ".

Signed and Sealed this

Third Day of October, 1995

Attest:

BRUCE LEHMAN

Attesting Officer     Commissioner of Patents and Trademarks